United States Patent [19]

Bentz et al.

[11] 3,940,376
[45] Feb. 24, 1976

[54] PERMANENTLY ANTISTATIC SHAPED STRUCTURES OF ACRYLONITRILE POLYMERS

[75] Inventors: Francis Bentz, Cologne; Gunther Nischk, Dormagen, both of Germany

[73] Assignee: Bayer Aktiengesellschaft, Leverkusen, Germany

[22] Filed: Nov. 25, 1974

[21] Appl. No.: 527,073

[30] Foreign Application Priority Data
Nov. 30, 1973 Germany............................ 2359658

[52] U.S. Cl...... 260/79.3 M; 260/80.72; 260/80.73; 260/80.77; 260/80.81; 260/85.5 R; 260/85.5 ES; 260/85.5 XA; 260/85.5 S; 260/85.5 AM; 260/88.7 R; 260/88.7 B; 260/DIG. 19
[51] Int. Cl.² ................ C08F 28/00; C08F 120/42; C08F 220/42; C08F 220/70
[58] Field of Search ........ 260/79.3 M, 80.72, 80.13, 260/80.81, 80.71, 85.5 R, 85.5 ES, 85.5 AM, 85.5 B, 85.5 XA, 85.5 S, 88.7 R, 88.7 B, DIG. 19

[56] References Cited
UNITED STATES PATENTS
3,847,884  11/1974  Radlmann et al............. 260/85.5 R
3,852,255  12/1974  Bentz et al..................... 260/88.7 R

*Primary Examiner*—Joseph L. Schofer
*Assistant Examiner*—Herbert J. Lilling
*Attorney, Agent, or Firm*—Plumley & Tyner

[57] ABSTRACT

The invention relates to shaped articles of acrylonitrile polymers which comprise as an antistatically active additive from 0.5 to 15 % by weight of at least one compound of the general formula

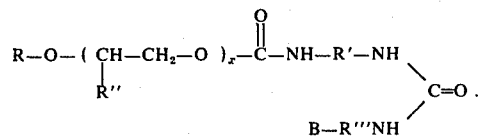

5 Claims, No Drawings

PERMANENTLY ANTISTATIC SHAPED STRUCTURES OF ACRYLONITRILE POLYMERS

This invention relates to permanently antistatic shaped structures, more especially filaments, fibres and films, of acrylonitrile polymers, and to a process for their production.

If the surface resistance of fibres based on acrylonitrile polymers exceeds $10^{12}$ ohms, it is often difficult or even impossible to use textiles produced from these products.

Processes by which the electrostatic charging of shaped structures of the kind in question can be reduced, are described in the literature. Thus, the electrical conductivity of fibres or of the textile products produced from them can be increased, for example, by surface treatment with antistatic preparations. Unfortunately, the antistatic effect imparted by this process is not permanent and disappears after only a few washes.

According to other literature, an antistatic finish can be obtained by applying aqueous solutions of suitable agents to the fibres in their aquagel form. Another method of reducing the electrostatic charging of shaped structures of synthetic polymers is to add polyethers or other suitable compounds to a solution or melt of these polymers before shaping. Unfortunately, most additives have the disadvantage of not being laundry-stable. It has already been proposed to add compounds obtained by reacting ethoxylated alcohols and diisocyanates to fibres of polyacrylonitrile so as to impart a permanent antistatic finish.

It has also been proposed to add to acrylonitrile polymers compounds which, in addition to a polyether group and two urethane groups, also contain a urea group, with a view to providing fibres of these polymers with an even better antistatic finish. Compounds of the kind in question correspond to the following general formula

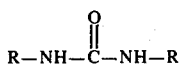

in which

R contains a polyether and a urethane group.

Accordingly, the compounds in question are symmetrical N,N'-disubstituted ureas.

It has now been found that compounds which, in addition to a polyether group and a urethane group, also contain a urea group, provide fibres of polyacrylonitrile with outstanding antistatic behaviour. The compounds in question are asymmetrical N,N'-disubstituted ureas.

It has also been found that compounds which, in addition to a polyether group and two urethane groups, additionally contain two urea groups provide fibres of polyacrylonitrile with extremely good antistatic behaviour.

Accordingly, the invention relates to a shaped article of an acrylonitrile polymer with at least one antistatic additive, comprising (A) 85 to 99.5 % by weight of an acrylonitrile copolymer consisting of at least 60 % by weight of copolymerised acrylonitrile and (B) of 0.5 to 15 % by weight of at least one compound corresponding to the general formula (I)

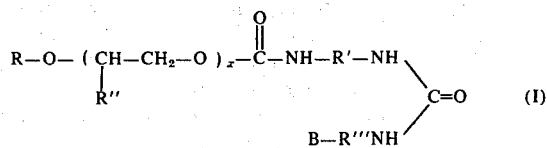

in which

R represents a $C_8$–$C_{18}$-alkyl, cycloalkyl, aryl, aralkyl or alkaryl radical optionally substituted by halogen or alkyl, x is an integer from 5 to 50, R' represents an alkylene, arylene, aralkylene, alkarylene, cycloalkylene radical, R'' represents hydrogen or a methyl group, B represents hydrogen or the group

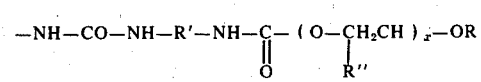

R''', where B is hydrogen, represents a $C_6$–$C_{12}$-arylene radical optionally substituted by halogen or alkyl, a $C_3$–$C_{17}$-alkylene radical or a cycloaliphatic radical, and, where B has the meaning different from hydrogen, R''' represents a $C_2$–$C_6$-alkylene radical, a $C_6$–$C_{12}$-arylene radical optionally substituted by halogen or alkyl or a cycloaliphatic radical.

The invention also relates to a process for the production of shaped structures of acrylonitrile copolymers with antistatic additives, in which at least one compound of the above general formula is added to a solution of an acrylonitrile polymer in an organic solvent, and the solvent is removed during shaping. The polyether-urethane-urea compound corresponding to the above general formula is added in a quantity of from 0.5 to 15 % by weight (based on the polymer mixture).

The antistatically active compounds being used according to the invention are not only highly compatible with the polymers, they are also highly resistant to washing by virtue of the urea group. They impart outstanding antistatic behaviour to fibres of acrylonitrile polymers.

In the context of the invention, shaped structures are primarily filaments, fibres and films. The compounds according to the invention are preferably added in a quantity of from 2 to 10 % by weight, based on the polymer mixture.

The group of acrylonitrile polymers includes, in particular, polyacrylonitrile or copolymers of acrylonitrile with (meth)acrylic acid esters, for example, (meth)acrylic acid methyl and ethyl ester; (meth)acrylamides, for example, (meth)acrylamide and N,N-dimethyl(meth)acrylamide; N-vinyl lactams, for example, N-vinylpyrrolidone, vinyl-, (meth)allyl esters or ethers; vinyl(idene) halides, for example, vinyl(idene)chloride and vinyl(idene)bromide; alkylvinylpyridine, for example, N-vinyl-4-methylpyridine; vinylimidazoles; (mono)dialkylaminoalkyl(meth)acrylates, for example, dimethylaminoethyl(meth)acrylate and their quaternised derivatives; vinyl-, (meth)allyl sulphonic acids, vinyl-, (meth)allyl phosphonic acids or their esters, etc., containing at least 60 % by weight of acrylonitrile in copolymerised form.

To produce the aforementioned additives, polyether monourethanes containing a free isocyanate group are initially prepared by methods known per se: to this end, aliphatic alcohols or phenols such as, 1-nonanol, 1-dodecanol, myristyl alcohol, cetylalcohol, stearyl alcohol and o-nonylphenol, are reacted in the melt with alkylene oxides, preferably ethylene oxide, in the presence of a basic catalyst, for example an alkali hydroxide such as sodium hydroxide or potassium hydroxide. 1 mol of the corresponding alcohol or phenol is reacted with 5 to 50 mols, preferably with 10 to 35 mols, of alkylene oxide. The polyalkoxylated alcohols thus obtained can readily be reacted with diisocyanates by a one-pot process, preferably after their OH-number has been determined. The reaction is carried out either in the melt at a temperature in the range of from 70° to 150°C, preferably at a temperature of from 90° to 130°C, or in an inert solvent, for example dimethylformamide, at the same temperatures. The alkylated alcohol is preferably reacted with the diisocyanate in a molar ratio of from 1 : 1 to 1 : 1.2. The reaction time ranges from 30 minutes to 12 hours, preferably from 1 to 7 hours. Initially the reaction gives a compound with a free isocyanate group corresponding to the formula:-

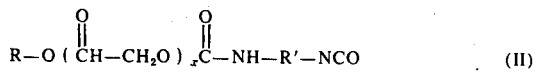

in which R, R', R'' and x are as previously defined.

Preferred diisocyanates are hexamethylene diisocyanate, cyclohexane-1,4-diisocyanate, 3-isocyanatomethyl-3,5,5-trimethylcyclohexane isocyanate, 1,3-phenylene diisocyanate, 1,4-phenylene diisocyanate, diphenylmethane-4,4'-diisocyanate, 2,2-bis-(4-isocyanatophenyl)-propane and 1,4-naphthylene diisocyanate.

The corresponding urea derivative is obtained from the compound containing a free isocyanate group in a one-pot process by adding the stoichiometric quantity of a monoamine or diamine. Following this addition, the reaction mixture is stirred for several hours at an elevated temperature in order to complete the reaction.

The following amines can be used for the preparation of compounds corresponding to the above general formula in which B is halogen: aniline, 2-chloraniline, 3-chloraniline, 4-chloraniline, cyclohexylamine, n-propylamine, N-butylamine, isobutylamine, stearyl amine, 3-aminotoluene, 6-chlor-3-aminotoluene and 4-chlor-3-aminotoluene.

The molar ratio of the compound containing a free isocyanate group to the amine is preferably between 1 : 1 and 1 : 1.2 or 1.2 : 1. The reaction timee ranges from 30 minutes to 12 hours, preferably from 1 to 7 hours.

The following diamines, for example, are used in the preparation of compounds corresponding to the above general formula (I) in which B has the meaning different from hydrogen: ethylene diamine, 1,6-hexamethylene diamine, 1,4-tetramethylene diamine, p-phenylene diamine, m-phenylene diamine and 4,4'-diaminodiphenylmethane.

The molar ratio of the compound containing a free isocyanate group to the diamine is preferably 2 : 1. It is of course also possible to use a slight excess (up to 10 %) of one of the two components.

The compounds corresponding to the above general formula can readily be obtained by a one-pot process: following preparation of the compounds containing a free isocyanate group by reacting a polyether having a free OH-group with a diisocyanate, the compounds corresponding to the above general formula are obtained, as described above, by adding a monoamine or diamine in a molar ratio of from 1 : 1 or 2 : 1. In both cases, the reaction is carried out in an organic, polar solvent, for example, dimethylacetamide. The solutions of the compounds thus obtained are directly added to the spinning solutions of the acrylonitrile polymer in the required quantity.

The surface resistance of the shaped structures, especially the fibres, as quoted in the Examples, was determined using a standard high-ohmmeter between the plates of two electrodes with a clearance of 1 cm at a measuring voltage of 100 V, in accordance with DIN 54 345 (Draft). To this end, the fibre material was conditioned for 72 hours under standard climatic conditions (50 % relative humidity, temperature 23°C) before each determination. Fibres produced in accordance with the invention have an electrical surface resistance at 23°C/50 % relative humidity of from about $10^{10}$ to $10^{11}$ ohms.

The fibres aaccording to the invention can be dyed with the usual dyes without any reduction in their outstanding antielectrostatic character.

In the following Examples which are to further illustrate the invention without limiting it, parts by weight are to parts by volume as kilogrammes to liters.

EXAMPLE 1 a. Preparation of

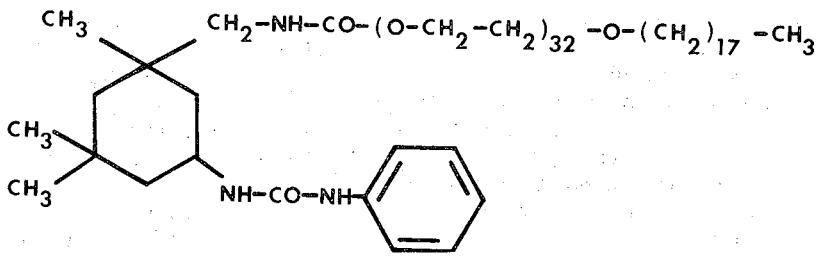

270 parts by weight of stearyl alcohol and 4 parts by weight of NaOH were introduced into a three-necked flask equipped with a stirrer and a reflux condenser. After the air in the flask had been displaced by nitrogen, ethylene oxide was introduced at 130° C up to an increase in weight of 1410 parts by weight. The molecular weight was determined by determining the OH-number. OH % = 1.01.

For neutralization, 60 parts by weight of pure acetic acid were added to 1682 parts by weight of this polyether, followed by heating for 1 hour at 100°C. The excess acetic acid was removed in a water jet vacuum at an oil-bath temperature of 100°C. 222 parts by weight of 3-isocyanatomethyl-3,5,5-trimethylcyclohexane isocyanate were introduced in portions at this temperature under a nitrogen atmosphere. The reaction mixture was then stirred for 8 hours at 130°C. 2000 parts by volume of dimethylformamide were then added, followed by the dropwise addition at 120° to 130°C of a solution of 93 parts by weight of aniline in 200 parts by volume of dimethylformamide. The mixture was then stirred for 5 hours at 130°C.

b. Production and testing of polyacrylic fibres

The solution prepared in Example 1a was used to prepare a 29 % dimethylformamide solution consisting of a mixture of 90 % by weight of an acrylonitrile copolymer (94 % by weight of acrylonitrile, 5 % by weight of methylmethacrylate and 1 % by weight of 3-methacroyl amino benzene benzene disulphonmide) with a K-value (according to Fikentscher) of 80, and 10 % by weight of the polyethylene oxide monourethane urea. This solution was dry-spun with a ball-drop viscosity of about 75 to 80 seconds at 80°C (the ball-drop viscosity is the time which it takes a ball of V2 steel according to DIN 5401 to drop a marked distance of 7 cm through a tube with an internal diameter of 3 cm filled with the solution to be measured). Denier of the fibres: 3.3 dtex.

The antielectrostatic activity of the additive was determined by measuring the surface resistance of the fibres at 23°C/50 % relative humidity.

Surface resistance after 10 washes: $2.10^{10}$ ohms
Surface resistance after dyeing and 3 washes: $5.10^{9}$ ohms

EXAMPLE 2 a. Preparation of

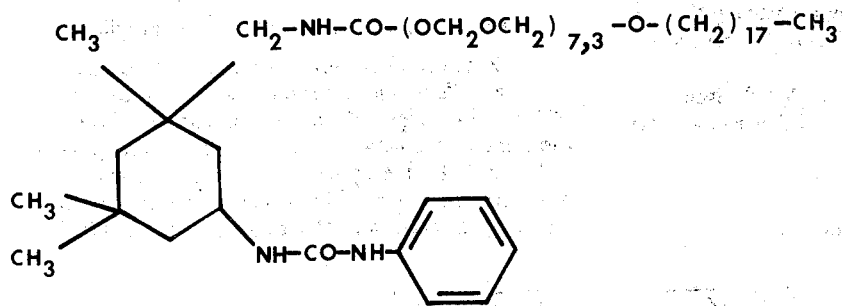

As in Example 1a, 270 parts by weight of stearyl alcohol were reacted with ethylene oxide at 100°C in the presence of 4 parts by weight of NaOH up to an increase in weight of 310 parts by weight (OH % = 2.88). After treatment with 60 parts by weight of pure acetic acid and removal of the excess acetic acid in vacuo, 222 parts by weight of 3-isocyanatomethyl-3,5,5-trimethylcyclohexane isocyanate were added at 100°C under nitrogen to 590 parts by weight of the polyether in the melt. This was followed by stirring for 6 hours at 130°C, after which 2000 parts by volume of dimethylformamide were added. 93 parts by weight of aniline were then added dropwise at 120°C. The reaction mixture was then stirred for 5 hours at 130°C in order to complete the reaction.

b. Production and testing of the polyacrylic fibres

This solution was used to prepare a 29 % dimethylformamide solution consisting of 95 % by weight of an acrylonitrile copolymer with the same composition as in Example 1 b and a K-value of 82, and 10 % by weight of the polyethylene oxide monourethane urea of Example 2a. The solution, which had a ball-drop viscosity of 75 to 80 seconds at 80°C, was dry spun. Denier of the fibres: 3.3 dtex.

Electrical surface resistance after 10 washes: $4.10^{10}$ ohms

Electrical surface resistance after dyeing and 3 washes: $5 . 10^{10}$ ohms

EXAMPLE 3 a. Preparation of

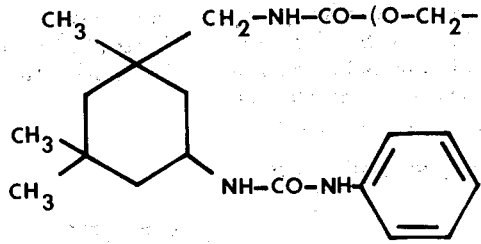

As in Example 1a, 880 parts by weight of ethylene oxide were added at 100°C to 270 parts by weight of stearyl alcohol in the presence of 4 parts by weight of NaOH (OH % = 1.48).

After treatment of the ethoxylated product with 60 parts by weight of acetic acid, and removal of the acetic acid in vacuo, 222 parts by weight of 3-isocyanatomethyl-3,5,5-trimethylcyclohexane isocyanate were added to the melt at 100°C. After stirring for 8 hours at 130°C, 2000 parts by volume of dimethylformamide were added, followed by the dropwise addition of 93 parts by weight of aniline at 120°C. The reaction mixture was then stirred for 3 hours at 120° to 130°C.

b. Production and testing of the polyacrylic fibres

The solution of Example 3a was used to prepare a 29

% dimethylformamide solution consisting of a mixture of 95 parts by weight of an acrylonitrile copolymer with the same composition as in Example 1b and a K-value of 82, and of 10 parts by weight of the polyethylene oxide monourethane urea. The solution has a ball-drop viscosity of about 80 seconds at 80°C. Denier of the fibres: 3.3 dtex. The surface resistance of the fibres was measured at 23°C/50 % relative humidity.

Surface resistance after 10 washes: $2.10^{10}$ ohms

Surface resistance after dyeing and 3 washes: $3.10^9$ ohms.

EXAMPLE 4 a. Preparation of

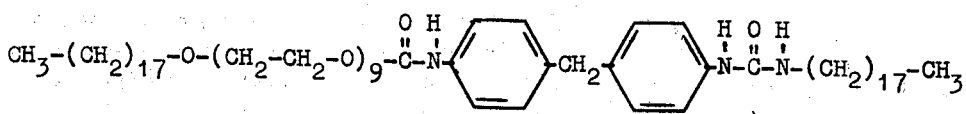

270 parts by weight of stearyl alcohol and solid NaOH were initially introduced into the reaction vessel. 400 parts by weight of ethylene oxide (OH % = 2.55) were introduced in the melt at around 100°C.

After treatment with acetic acid and concentration in vacuo, 125 parts by weight of 4,4'-diphenylmethane diisocyanate were introduced in portions at 130°C into 330 parts by weight of this product. After stirring for 5 hours at 130°C, the melt was diluted with 700 parts by volume of dimethylformamide. 135 parts by weight of stearylamine were introduced at 130°C and the solution subsequently heated under reflux for 5 hours.

b. Production and testing of polyacrylic fibres

The solution of 4a 4a was used to prepare a 29 % dimethylformamide solution consisting of a mixture of 90 % by weight of an acrylonitrile copolymer with the same composition as in Example 1b and a K-value of 83, and of 10 % by weight of the polyethylene oxide monourethane urea. The solution had a ball-drop viscosity of 75 to 80 seconds at 80°C. It is dry spun. Denier of the fibres: 3.3 dtex. The antielectrostatic activity of the additive is determined by measuring the surface resistance of the fibres at 23°C/50 % relative humidity.

Surface resistance after 10 washes: $5.10^9$ ohms

Surface resistance after dyeing and 3 washes: $1.10^9$ ohms

EXAMPLE 5 a. Preparation of

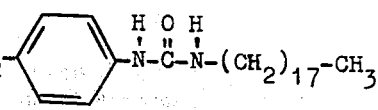

As in the preceding Examples, 270 parts by weight of stearyl alcohol were reacted with ethylene oxide at 100°C in the presence of 4 parts by weight of NaOH up to an increase in weight of 970 parts by weight (OH % = 1.37).

After treatment with acetic acid and removal of the excess acetic acid in vacuo, 315 parts by weight of the ethoxylated stearyl alcohol were reacted at 130°C with 360 parts by weight of 4,4'-diphenylmethane diisocyanate. This was followed by stirring for 5 hours at 130°C. Following the addition of 450 parts by volume of dimethylformamide to the melt, 67 parts by weight of stearylamine were introduced in portions. This was followed by heating under reflux for 5 hours.

b. Production and testing of polyacrylic fibres

The solution of Example 5a was used to prepare a 29 % dimethylformamide solution consisting of a mixture of 90 % by weight of an acrylonitrile copolymer with the same composition as in Example 1b and a K-value of 80, and 10 parts by weight of the polyethylene oxide monourethane urea prepared in accordance with Example 5a. The solution had a ball-drop viscosity of about 80 seconds at 80°C. Denier of the fibres: 3.3 dtex. After 10 washes, the surface resistance of the fibres at 23°C/50 % relative humidity amounts to $7.10^9$ ohms and, after dyeing and 3 washes to $3.10^{10}$ ohms.

EXAMPLE 6 a. Preparation of

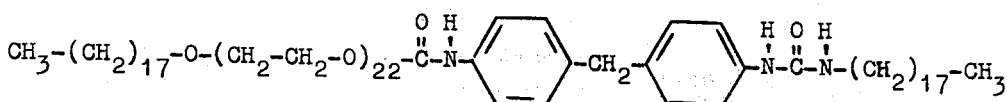

420 parts by weight of the ethoxylated stearyl alcohol of Example 1were reacted in the melt at 130°C with 63 parts by weight of 4,4'-diphenylmethane diisocyanate. The melt was then stirred for 5 hours at 130°C. After dilution with 550 parts by volume of dimethylformamide, 67 parts by weight of stearylamine were added to the solution and the resulting solution was heated under reflux for 5 hours.

b. Production and testing of the polyacrylic fibres

The solution of Example 6a was used to prepare a 29 % dimethylformamide solution consisting of a mixture of 90 % by weight of an acrylonitrile copolymer with the same composition as in Example 1b and a K-value of 81, and of 10 % by weight of the polyethylene oxide monourethane urea. The viscosity determined by the ball-drop method was 75 and 80 seconds at 80°C. The solution was dry spun. Denier of the fibres: 3.3 dtex. After 10 washes, the surface resistance of the fibres at 23°C/50 % relative humidity amounts to $6.10^{10}$ ohms and, after dyeing and 3 washes, to $1.10^{10}$ ohms.

EXAMPLE 7 a. Preparation of

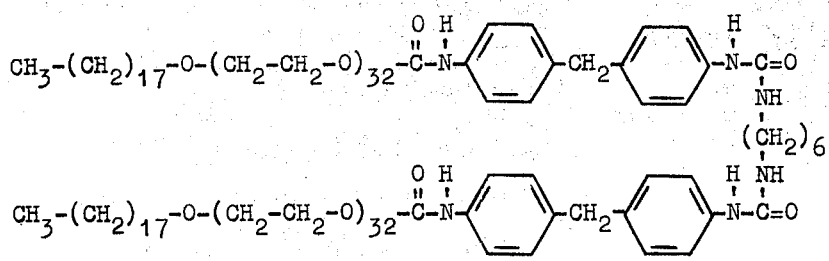

420 parts by weight of the ethoxylated stearyl alcohol described in Example 1a were dissolved in 500 parts by volume of dimethylformamide. 63 parts by weight of 4,4' diphenylmethane diisocyanate were introduced in portions at 100°C. The solution was stirred for 3 hours at 130°C. 15 parts by weight of ethylene diamine were then added dropwise at 100°C. The solution was heated under reflux for 3 to 5 hours.

b. Production and testing of the polyacrylic fibres

The solution of Example 7a was used to prepare a 29 % dimethylformamide solution consisting of a mixture of 92.5 % by weight of an acrylonitrile copolymer with the same composition as in Example 1b and a K-value of 80, and of 7.5 % by weight of the polyethylene oxide diurethane diurea. The solution had a ball-drop viscosity of 75 to 80 seconds at 80°C. It was dry spun. Denier of the fibres: 3.3 dtex. The antielectrostatic activity of the addition was determined by measuring the surface resistance of the fibres at 23°C/50 % relative humidity.

Surface resistance after 10 washes: $5.10^{10}$ ohms

Surface resistance after dyeing and 3 washes: $2.10^{10}$ ohms

EXAMPLE 8 a. Preparation of

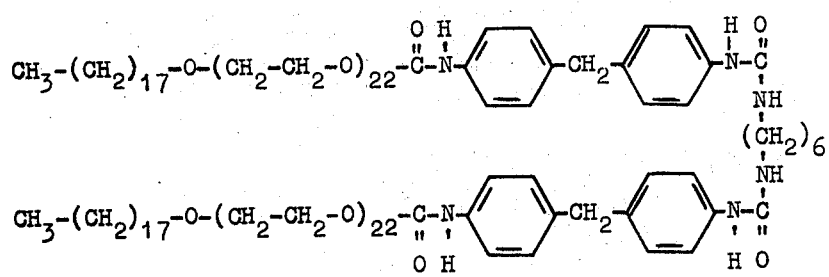

315 parts by weight of the ethoxylated stearyl alcohol described in Example 5a were dissolved in 396 parts by volume of dimethylformamide. 360 parts by weight of 4,4'-diphenylmethane diisocyanate were added to this solution at 100°C. This was followed by stirring for 3 hours at 130°C, after which 15 parts by weight of ethylene diamine were added dropwise. The solution was then boiled under reflux for 3 to 5 hours.

b. Production and testing of the polyacrylic fibres

The solution of Example 8a was used to prepare a 29 % dimethylformamide solution consisting of a mixture of 95 % by weight of an acrylonitrile copolymer with the same composition as in Example 1b and a K-value of 81, and of 5 % by weight of the polyethylene oxide diurethane diurea. Ball-drop viscosity of the solution: 75 to 80 seconds at 80°C. The solution was dry spun. Denier of the fibres: 3.3 dtex. After 10 washes, the surface resistance of the fibres at 23°C/50 % relative humidity was $1.10^{10}$ ohms and, after dyeing and 3 washes, $5.10^{9}$ ohms.

EXAMPLE 9 a. Preparation of

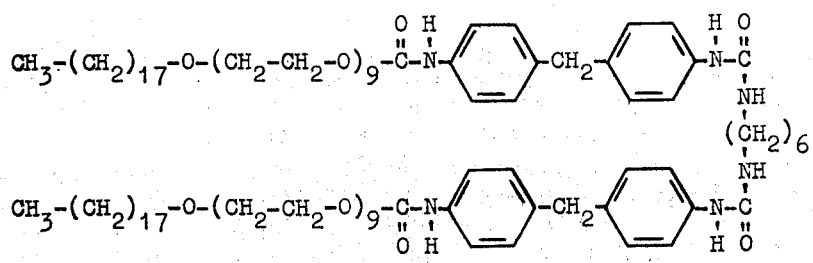

The stearyl alcohol described in Example 4a was used as the ethoxylated product. 330 parts by weight of this compound were dissolved in 485 parts by volume of dimethylformamide, followed by the dropwise addition in portions at 100°C of 125 parts by weight of 4,4'-diphenylmethane diisocyanate. The mixture was stirred for 3 hours at 130°C, after which 30 parts by weight of ethylene diamine are added dropwise to it at 100°C. The solution was then heated under reflux for 3 to 5 hours.

b. Production and testing of the polyacrylic fibres

The solution of Example 9a was used to prepare a 29 % dimethylformamide solution consisting of a mixture of 95 parts by weight of an acrylonitrile copolymer with the same composition as in Example 1b and a K-value of 85, and 5 parts by weight of the additive. The spinning solution has a ball-drop viscosity of 75 to 80 seconds at 80°C. The solution is dry spun. Denier of the fibres: 3.3 dtex. After 10 washes, the surface resistance of the fibres at 23°C/50 % relative humidity amounts to $2.10^{10}$ ohms and, after dyeing and 3 washes, to $6.10^9$ ohms.

EXAMPLE 10 a. Preparation of

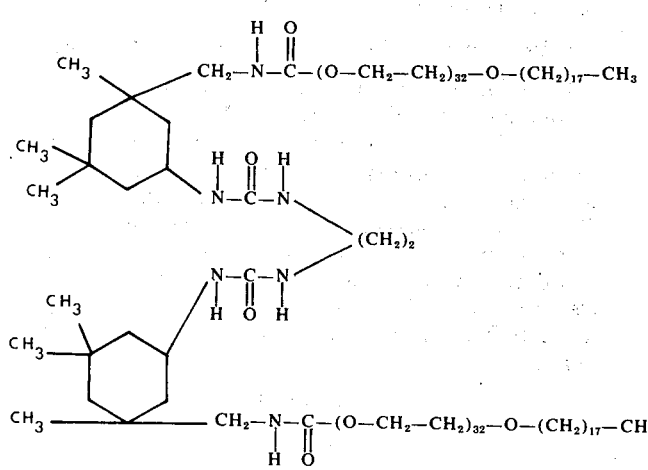

Stearyl alcohol was ethoxylated in the same way as in Example 1a). 56 parts by weight of 3-isocyanatomethyl-3,5,5-trimethylcyclohexane isocyanate were added dropwise at 100°C to 420 parts by weight of the ethoxylated stearyl alcohol. This was followed by stirring for 3 hours at 130°C. Following the addition of 500 parts by volume of dimethylformamide, 15 parts by weight of ethylene diamine were added dropwise and the solution was heated under reflux for 5 hours.

b. Production and testing of the polyacrylic fibres

The solution of Example 10a was used to prepare a 29 % dimethylformamide solution consisting of a mixture of 95 % by weight of acrylonitrile copolymer with the same composition as in Example 1b and a K-value of 83, and 5 % by weight of the polyethylene oxide diurethane diurea. The solution had a ball-drop viscosity of 75 to 80 seconds at 80°C. It was dry spun. Denier of the fibres: 3.3 dtex. After 10 washes, the surface resistance of the fibres at 23°C/50 % relative humidity was $9.10^9$ ohms and, after dyeing and 3 washes, $6.10^9$ ohms.

EXAMPLE 11 a. Preparation of

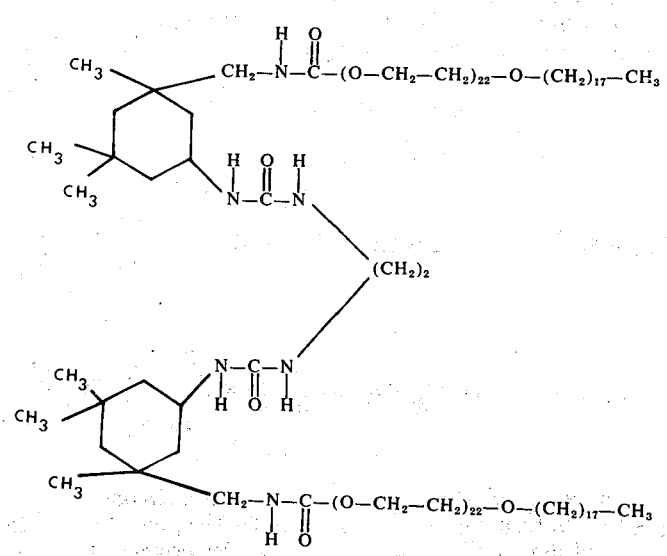

56 parts by weight of 3-isocyanatomethyl-3,5,5-trimethylcyclohexane isocyanate were added dropwise at 100°C to 319 parts by weight of the ethoxylated stearyl alcohol described in Example 5a. After heating for 3 hours at 130°C, the reaction mixture was diluted with 400 parts by volume of dimethylformamide, followed by the dropwise addition of 15 parts by weight of ethylene diamine. The solution was then heated under reflux for 3 hours.

b. Production and testing of the polyacrylic fibres

The solution of the product described in Example 11a was used to prepare a 29 % dimethylformamide solution consisting of a mixture of 95 % by weight of an acrylonitrile copolymer with the same composition as in Example 1b and a K-value of 81, and of 5 % by weight of the polyethylene oxide diurethane diurea. The spinning solution had a ball-drop viscosity of 75 to 80 seconds at 80°C. It was dry spun. Denier of the fibres; 3.3 dtex. After 10 washes, the surface resistance of the fibres at 23°C/50 % relative humidity was $1.10^{10}$ ohms and, after dyeing and 3 washes, $7.10^9$ ohms.

EXAMPLE 12 a. Preparation of

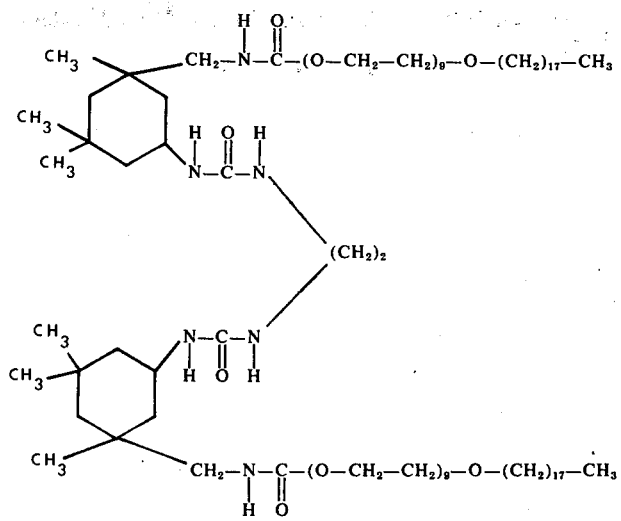

Following the dropwise addition of 111 parts by weight of 3-isocyanatomethyl-3,5,5-trimethylcyclohexane isocyanate to 330 parts by weight of the ethoxylated stearyl alcohol described in Example 4a, the melt was heated for 3 hours at 130°C. The melt was then diluted by the addition of 471 parts by volume of dimethylformamide, after which 30 parts by weight of ethylene diamine were added dropwise at 100°C. The reaction was completed by heating under reflux for 5 hours.

b. Production and testing of polyacrylic fibres

The solution of Example 12a was used to prepare a 29 % dimethylformamide solution consisting of a mixture of 92.5 % by weight of acrylonitrile copolymer with the same composition as in Example 1b and a K-value of 80, and 7.5 % by weight of the polyethylene oxide diurethane diurea. The spinning solution had a ball-drop viscosity of 75 to 80 seconds at 80°C. The solution was dry-spun. Denier of the fibres: 3.3 dtex. After 10 washes, the surface resistance of the fibres at 23°C/50 % relative humidity amounted to $7.10^9$ ohms and, after dyeing and 3 washes, to $3.10^9$ ohms.

What we claim is:

1. A shaped article of an acrylonitrile polymer with at least one antistatic additive, comprising (A) 85 to 99.5 % by weight of an acrylonitrile copolymer consisting of at least 60 % by weight of copolymerised acrylonitrile and (B) of 0.5 to 15 % by weight of at least one compound corresponding to the general formula (I)

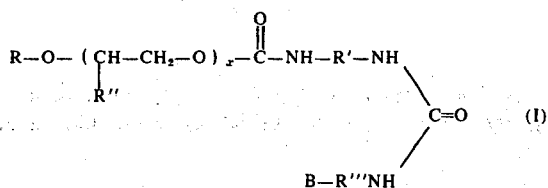

in which

R represents a $C_8$–$C_{18}$-alkyl, cycloalkyl, aryl, aralkyl or alkaryl radical optionally substituted by halogen or alkyl, $a$ is an integer from 5 to 50, R' represents ann alkylene, arylene, aralkylene, alkarylene, cycloalkylene radical, R'' represents hydrogen or a methyl group, B represents hydrogen or the group

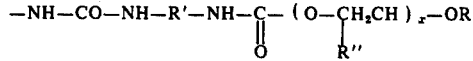

R''' , where B is hydrogen, represents a $C_6$–$C_{12}$-arylene radical optionally substituted by halogen or alkyl, a $C_3$–$C_{17}$-alkylene radical or a cycloaliphatic radical, and, where B has the meaning different from hydrogen, R''' represents a $C_2$–$C_6$-alkylene radical, a $C_6$–$C_{12}$-arylene radical optionally substituted by halogen or alkyl or a cycloaliphatic radical.

2. The shaped article of claim 1, wherein, in said general formula the radical, R' represents the radical

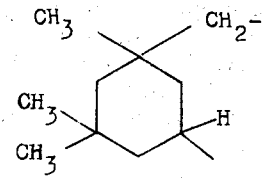

3. The shaped article of claim 1, wherein, in said general formula the radical R' represents the radical

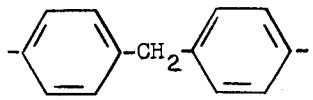

4. A process for the production of an shaped article as claimed in claim 1 which comprises adding as an antistatic agent at least one compound corresponding to the general formula

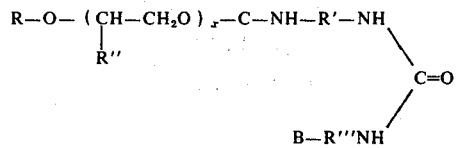

in which
x, R, R'', R ''' and B are as defined in claim 1 in an amount of from 0.5 to 15 % by weight (based on the polymer mixture) to a solution of an acrylonitrile polymer in an organic solvent and removing said solvent during shaping said acrylonitrile polymer consisting of at least 60 % by weight of acrylonitrile.

5. A shaped article when containing a compound of to the general formula

R—O—(CH—CH$_2$O)$_x$—C—NH—R'—NH\
       |                              \
       R''                             C=O
                                      /
                              B—R'''NH in which R, R', R'', R''', x and B are as defined in claim 1.

* * * * *